(12) United States Patent
Nguyen et al.

(10) Patent No.: US 10,813,749 B2
(45) Date of Patent: Oct. 27, 2020

(54) DOCKING DEVICE MADE WITH 3D WOVEN FABRIC

(71) Applicant: Edwards Lifesciences Corporation, Irvine, CA (US)

(72) Inventors: Son V. Nguyen, Irvine, CA (US); Kevin D. Rupp, Irvine, CA (US); Ajay Chadha, Irvine, CA (US); Jeff Lindstrom, Coto de Caza, CA (US)

( * ) Notice: Subject to any disclaimer, the term of this patent is extended or adjusted under 35 U.S.C. 154(b) by 0 days.

(21) Appl. No.: 15/841,046

(22) Filed: Dec. 13, 2017

(65) Prior Publication Data

US 2018/0168804 A1 Jun. 21, 2018

Related U.S. Application Data

(60) Provisional application No. 62/436,866, filed on Dec. 20, 2016.

(51) Int. Cl.
*A61F 2/24* (2006.01)
*D03D 15/00* (2006.01)
(Continued)

(52) U.S. Cl.
CPC ............. *A61F 2/2409* (2013.01); *D03D 3/02* (2013.01); *D03D 15/00* (2013.01); *D03D 25/005* (2013.01);
(Continued)

(58) Field of Classification Search
CPC ................. A61F 2/2409; A61F 2/2418; A61F 2210/0014; A61F 2210/0071;
(Continued)

(56) References Cited

U.S. PATENT DOCUMENTS 1,392,535 A * 10/1921 Stevenson ............... B29C 70/24
442/206
3,971,670 A * 7/1976 Homsy ..................... A61F 2/08
156/196
(Continued)

FOREIGN PATENT DOCUMENTS

DE 19532846 A1 3/1997
DE 19907646 A1 8/2000
(Continued)

*Primary Examiner* — Paul B Prebilic
(74) *Attorney, Agent, or Firm* — Chang & Hale LLP; Hans P. Smith

(57) ABSTRACT

A docking device for a bioprosthesis is disclosed that can change shape and recover after a deforming stress is removed, that adjusts to surrounding conditions to accommodate different complex anatomic geometries, and that mitigates leakage around the bioprosthesis. The docking device can include a 3D woven fabric forming an internal surface, an outer surface, and a thickness therebetween. A filler can be coupled to the outer surface. A method for making a docking device is also provided. The method includes weaving a 3D woven fabric by interlacing a shape memory material, a low-melt thermoplastic polymer or resin having a melting point, and a high-tenacity biocompatible material; and pressing and heating the 3D woven fabric over a shape-setting mold at temperatures greater than the melting point of the low-melt thermoplastic polymer or resin.

16 Claims, 5 Drawing Sheets

(51) Int. Cl.
*D03D 25/00* (2006.01)
*D03D 3/02* (2006.01)
(52) U.S. Cl.
CPC ..... *A61F 2/2418* (2013.01); *A61F 2210/0019* (2013.01); *A61F 2210/0071* (2013.01); *A61F 2210/0076* (2013.01); *A61F 2220/0075* (2013.01); *A61F 2230/0069* (2013.01); *A61F 2240/004* (2013.01); *A61F 2250/006* (2013.01); *A61F 2250/0069* (2013.01); *D10B 2509/00* (2013.01)
(58) Field of Classification Search
CPC ...... A61F 2210/0076; A61F 2220/0008; A61F 2230/0065; A61F 2250/0069; D03D 25/005; D03D 3/02; D03D 15/00; D03D 15/02; D03D 2700/0111; D03D 2700/0137; D03D 2700/0144; D03D 2270/0174
USPC .................................. 442/204–216
See application file for complete search history.

(56) References Cited

U.S. PATENT DOCUMENTS

| | | | |
|---|---|---|---|
| 4,035,849 A | | 7/1977 | Angell et al. |
| 4,187,618 A | * | 2/1980 | Diehl ............... D21F 7/083 139/383 A |
| 4,615,256 A | * | 10/1986 | Fukuta ............ D03D 41/004 139/11 |
| 4,854,352 A | * | 8/1989 | Combier ........... D03D 11/00 139/408 |
| 5,059,177 A | | 10/1991 | Towne et al. |
| 5,104,406 A | * | 4/1992 | Curcio ............ A61F 2/2409 623/2.39 |
| 5,399,418 A | * | 3/1995 | Hartmanns ........... B64G 6/00 139/420 R |
| 5,411,552 A | | 5/1995 | Andersen et al. |
| 5,478,638 A | * | 12/1995 | Springer ............ B32B 25/02 442/205 |
| 5,554,185 A | | 9/1996 | Block et al. |
| 5,571,175 A | * | 11/1996 | Vanney ............ A61F 2/2409 623/2.41 |
| 5,711,960 A | | 1/1998 | Shikinami |
| 5,840,081 A | | 11/1998 | Andersen et al. |
| 6,168,614 B1 | | 1/2001 | Andersen et al. |
| 6,419,696 B1 | | 7/2002 | Ortiz et al. |
| 6,432,134 B1 | | 8/2002 | Anson et al. |
| 6,458,153 B1 | | 10/2002 | Bailey et al. |
| 6,527,979 B2 | | 3/2003 | Constantz et al. |
| 6,582,462 B1 | | 6/2003 | Andersen et al. |
| 6,652,578 B2 | | 11/2003 | Bailey et al. |
| 6,730,121 B2 | | 5/2004 | Ortiz et al. |
| 6,797,002 B2 | | 9/2004 | Spence et al. |
| 6,908,481 B2 | | 6/2005 | Cribier |
| 7,018,408 B2 | | 3/2006 | Bailey et al. |
| 7,037,334 B1 | | 5/2006 | Hlavka et al. |
| 7,077,861 B2 | | 7/2006 | Spence |
| 7,101,395 B2 | | 9/2006 | Tremulis et al. |
| 7,125,421 B2 | | 10/2006 | Tremulis et al. |
| 7,585,321 B2 | | 9/2009 | Cribier |
| 7,618,446 B2 | | 11/2009 | Andersen et al. |
| 7,737,060 B2 | | 6/2010 | Strickler et al. |
| 7,785,366 B2 | | 8/2010 | Maurer et al. |
| 7,951,195 B2 | | 5/2011 | Antonsson et al. |
| 8,323,335 B2 | | 12/2012 | Rowe et al. |
| 8,377,115 B2 | | 2/2013 | Thompson |
| 8,398,708 B2 | | 3/2013 | Meiri et al. |
| 8,449,605 B2 | | 5/2013 | Lichtenstein et al. |
| 8,449,606 B2 | | 5/2013 | Eliasen et al. |
| 8,657,872 B2 | | 2/2014 | Seguin |
| 8,663,322 B2 | | 3/2014 | Keranen |
| 8,672,998 B2 | | 3/2014 | Lichtenstein et al. |
| 8,734,507 B2 | | 5/2014 | Keranen |
| 9,078,747 B2 | | 7/2015 | Conklin |
| 9,095,434 B2 | | 8/2015 | Rowe |
| 9,119,718 B2 | | 9/2015 | Keranen |
| 9,237,886 B2 | | 1/2016 | Seguin et al. |
| 9,364,326 B2 | | 6/2016 | Yaron |
| 9,463,268 B2 | | 10/2016 | Spence |
| 9,474,599 B2 | | 10/2016 | Keranen |
| 9,622,863 B2 | | 4/2017 | Karapetian et al. |
| 10,179,043 B2 | * | 1/2019 | Cohen-Tzemach ......... A61F 2/2418 |
| 2003/0225420 A1 | | 12/2003 | Wardle |
| 2004/0260389 A1 | | 12/2004 | Case et al. |
| 2005/0096736 A1 | | 5/2005 | Osse et al. |
| 2005/0119735 A1 | | 6/2005 | Spence et al. |
| 2005/0137691 A1 | | 6/2005 | Salahieh et al. |
| 2005/0203614 A1 | | 9/2005 | Forster et al. |
| 2005/0203617 A1 | | 9/2005 | Forster et al. |
| 2006/0004442 A1 | * | 1/2006 | Spenser ............ A61F 2/2409 623/2.11 |
| 2006/0025857 A1 | | 2/2006 | Bergheim et al. |
| 2007/0203575 A1 | | 8/2007 | Forster et al. |
| 2007/0265700 A1 | | 11/2007 | Eliasen et al. |
| 2007/0293927 A1 | | 12/2007 | Frank et al. |
| 2008/0033542 A1 | | 2/2008 | Antonsson et al. |
| 2008/0125853 A1 | | 5/2008 | Bailey et al. |
| 2008/0208330 A1 | | 8/2008 | Keranen |
| 2010/0145440 A1 | | 6/2010 | Keranen |
| 2010/0312333 A1 | | 12/2010 | Navia et al. |
| 2010/0318184 A1 | | 12/2010 | Spence |
| 2010/0331972 A1 | * | 12/2010 | Pintor ............... A61F 2/2409 623/2.11 |
| 2012/0059458 A1 | | 3/2012 | Buchbinder et al. |
| 2013/0006279 A1 | | 1/2013 | Mortarino |
| 2013/0190857 A1 | * | 7/2013 | Mitra ............... A61L 27/16 623/1.23 |
| 2014/0074299 A1 | | 3/2014 | Endou et al. |
| 2014/0172070 A1 | | 6/2014 | Seguin |
| 2014/0277424 A1 | | 9/2014 | Oslund |
| 2014/0303719 A1 | * | 10/2014 | Cox ............... A61F 2/2418 623/2.11 |
| 2014/0379074 A1 | | 12/2014 | Spence et al. |
| 2015/0230921 A1 | | 8/2015 | Chau et al. |
| 2015/0282931 A1 | | 10/2015 | Brunnett et al. |
| 2015/0327999 A1 | | 11/2015 | Board et al. |
| 2015/0335428 A1 | | 11/2015 | Keranen |
| 2015/0374493 A1 | | 12/2015 | Yaron et al. |
| 2016/0074165 A1 | | 3/2016 | Spence et al. |
| 2016/0095705 A1 | | 4/2016 | Keranen et al. |
| 2016/0184095 A1 | | 6/2016 | Spence et al. |
| 2016/0199177 A1 | | 7/2016 | Spence et al. |
| 2016/0256276 A1 | | 9/2016 | Yaron |
| 2017/0007399 A1 | | 1/2017 | Keranen |
| 2017/0007402 A1 | | 1/2017 | Zerkowski et al. |
| 2019/0099265 A1 | * | 4/2019 | Braido ............ A61F 2/2409 |
| 2019/0226126 A1 | * | 7/2019 | Hozumi ............ D03D 9/00 |
| 2020/0141032 A1 | * | 5/2020 | Yoshikawa ......... D03D 11/00 |

FOREIGN PATENT DOCUMENTS

| | | |
|---|---|---|
| EP | 0592410 B1 | 10/1995 |
| EP | 0850607 A1 | 7/1998 |
| EP | 1432369 | 6/2004 |
| EP | 1521550 | 4/2005 |
| EP | 1827314 | 12/2010 |
| EP | 2620125 A1 | 7/2013 |
| EP | 2726018 | 5/2014 |
| EP | 2806829 | 12/2014 |
| WO | 9117720 A1 | 11/1991 |
| WO | 0149213 A2 | 7/2001 |
| WO | 0154625 A1 | 8/2001 |
| WO | 0247575 A2 | 6/2002 |
| WO | 2005084595 A1 | 9/2005 |
| WO | 2005102015 A2 | 11/2005 |
| WO | 2006011127 A2 | 2/2006 |
| WO | 2007067942 A1 | 6/2007 |
| WO | 2010121076 A2 | 10/2010 |
| WO | 2013110722 A2 | 8/2013 |
| WO | 2013114214 A2 | 8/2013 |

(56) References Cited

FOREIGN PATENT DOCUMENTS

| | | |
|---|---|---|
| WO | 2015023579 A1 | 2/2015 |
| WO | 2015023862 A2 | 2/2015 |
| WO | 2015127264 A1 | 8/2015 |
| WO | 2015198125 A1 | 12/2015 |
| WO | 2016038017 A1 | 3/2016 |
| WO | 2016040881 A1 | 3/2016 |
| WO | 2016130820 A1 | 8/2016 |

* cited by examiner

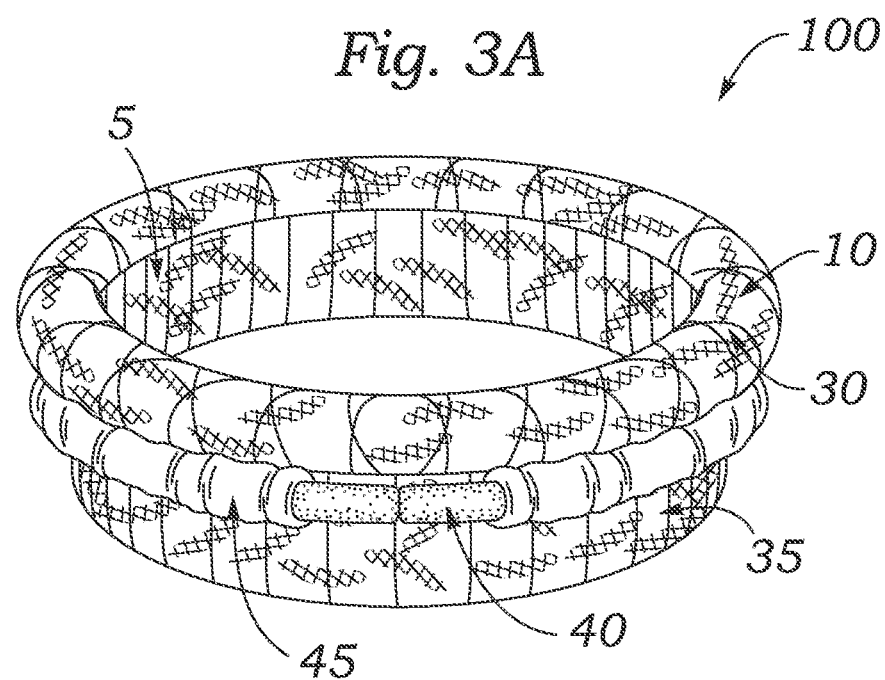
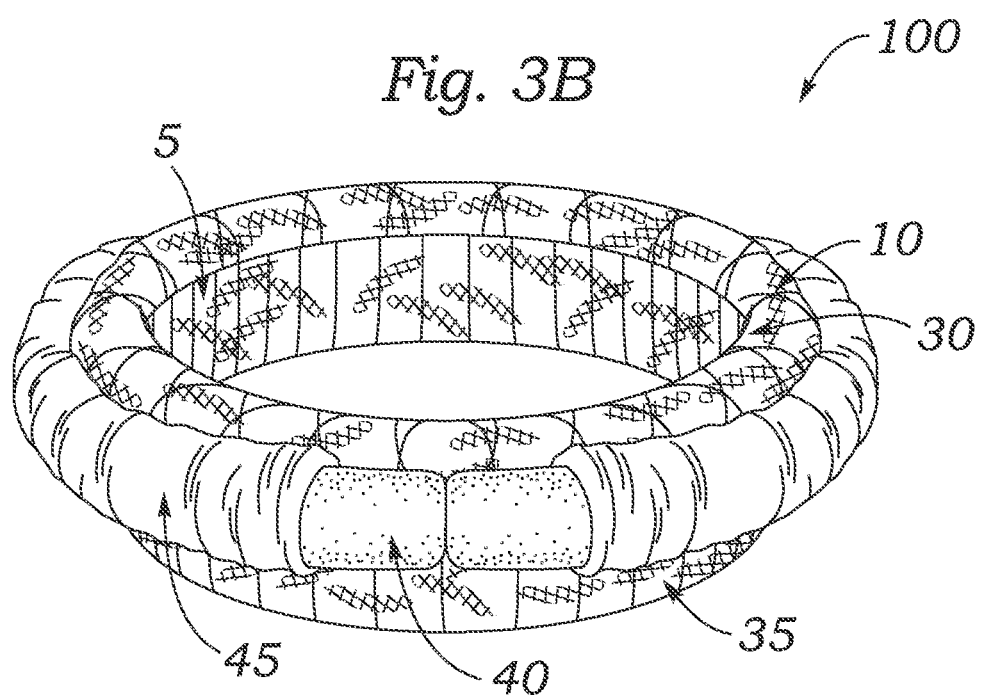

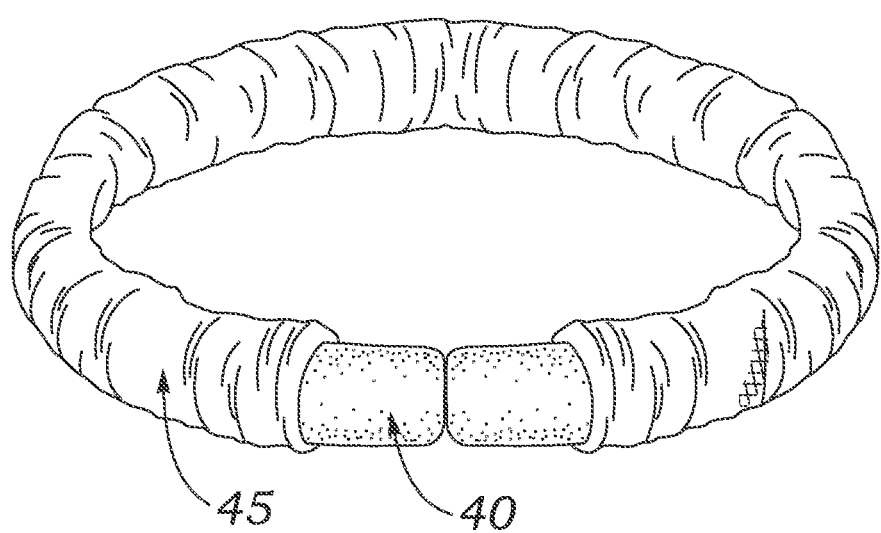

DOCKING DEVICE MADE WITH 3D WOVEN FABRIC

CROSS-REFERENCE TO RELATED APPLICATION(S)

This application claims priority to U.S. Provisional Application No. 62/436,866, filed on Dec. 20, 2016, and entitled DOCKING DEVICE MADE WITH 3D WOVEN FABRIC, the disclosure of which is hereby incorporated by reference in its entirety.

BACKGROUND

The unique geometry and sometimes irregular size of a patient's native heart valve anatomy present challenges to providing an implantable bioprosthetic heart valve that fits within and is provided in intimate contact or seal with the surrounding tissue.

SUMMARY

This summary is meant to provide some examples and is not intended to be limiting of the scope of the invention in any way. For example, any feature included in an example of this summary is not required by the claims, unless the claims explicitly recite the features. Also, the features described can be combined in a variety of ways. Various features and steps as described elsewhere in this disclosure may be included in the examples summarized here.

Examples are described herein relating to docking devices or docking stations for prostheses or bioprostheses, such as heart valves, including docking devices that include a three-dimensional (3D) woven fabric, and methods of making such docking devices.

For example, docking devices/docking stations herein can be a docking device for a prosthesis (e.g., a bioprosthesis). The docking devices comprise a 3D woven fabric forming a shaped element having an internal surface, an outer surface, and a thickness therebetween. The shaped element can be annuluar, and it can be undulating, zig zag, or straight. The shaped element can have a rectangular cross section or be concave, convex, or indented (other cross-section shapes are also possible). Preferably, the shaped element can be shaped to increase the internal surface area (e.g., with a rectangular, indented, or concave cross-section, for example, such that the shaped element is columnar or hourglass shaped) that can contact or otherwise interact with the prosthesis (e.g., bioprosthesis) to increase the retention forces. The docking station can include a filler structure coupled to the outer surface of the shaped element. The prosthesis can be a heart valve or transcatheter heart valve.

The 3D woven fabric of a docking device or docking station can comprise multiple different types of fibers or yarns, e.g., 2-10 different types of fibers or yarns. In certain embodiments, the 3D woven fabric of a docking station can comprise first, second, and third different types of fibers or yarns. For example, the first type of fiber or yarn can comprise a shape memory material, the second type of fiber or yarn can comprise a low-melt thermoplastic polymer or resin, and the third type of fiber or yarn can comprise a high-tenacity biocompatible material. In certain embodiments, the shape memory material comprises Nitinol. In certain embodiments, the low-melt thermoplastic polymer or resin has a melting point between 85 degrees Celsius and 200 degrees Celsius. For example, the low-melt thermoplastic polymer or resin can comprise Nylon. In certain embodiments, the high-tenacity biocompatible material comprises polyethylene terephthalate (PET).

If a filler structure is used/included, the filler structure can be covered with a material having low porosity and reduced permeability. In certain embodiments, the filler structure comprises polymer foam. For example, the polymer foam can be at least partially covered with a tubular woven fabric. In certain embodiments, the tubular woven fabric comprises PET.

The docking devices or docking stations can comprise additional features or components described elsewhere in this disclosure.

In one embodiment, a 3D woven fabric for a prosthesis docking device (e.g., a bioprosthesis docking device/station) comprises a shape memory material, a low-melt thermoplastic polymer or resin, and a high-tenacity biocompatible material. The shape memory material can comprise Nitinol. In certain embodiments, the low-melt thermoplastic polymer or resin has a melting point of 85 degrees Celsius to 200 degrees Celsius. The low-melt thermoplastic polymer or resin can comprise Nylon. The high-tenacity biocompatible material can comprise PET.

In some implementations, the present disclosure relates to a method for making a docking device for a prosthesis (e.g., a bioprosthesis). The method comprises weaving a 3D woven fabric by interlacing multiple portions (e.g., threads, yarns, etc.) together in a 3D woven pattern. In certain embodiments, the method includes weaving a 3D woven fabric by interlacing a shape memory material, a low-melt thermoplastic polymer or resin, and a high-tenacity biocompatible material. The method can include pressing and heating the 3D woven fabric over a shape-setting mold at temperatures greater than a melting point of the low-melt thermoplastic polymer or resin. In certain embodiments, the shape memory material comprises Nitinol, the low-melt thermoplastic polymer or resin comprises Nylon having a melting point of 85 degrees Celsius to 200 degrees Celsius, and the high-tenacity biocompatible material comprises polyethylene terephthalate (PET).

The method can further comprise attaching a filler structure to a surface of the 3D woven fabric. For example, attaching the filler structure can comprise sewing the filler structure to the surface of the 3D woven fabric. The method can further comprise covering the filler structure with a tubular woven fabric comprising PET, wherein the filler comprises polymer foam. The method(s) of manufacturing can include any of the above steps in combination with any other manufacturing or processing steps described elsewhere in this disclosure.

In some implementations, methods such as a method for replacing a native heart valve, a method of using a docking station, etc. can comprise one or more of the following:

(a) implanting a 3D woven fabric docking station at a native heart valve (the docking station can be the same as or similar to docking stations described above or elsewhere in this disclosure, e.g., the docking station can include a shape memory material, a low-melt thermoplastic polymer or resin, and a high-tenacity biocompatible material interlaced together);

(b) implanting a prosthesis/bioprosthesis (e.g., a prosthetic heart valve or transcatheter heart valve) inside the docking station at the native heart valve such that forces between the docking station and the prosthesis/bioprosthesis help to secure the prosthesis/bioprosthesis in the native heart valve (optionally, this can involve pinching tissue between the docking station and prosthesis/bioprosthesis, and/or using an attachment means such as anchor(s), adhesive(s), suture(s), clip(s), etc. to secure the docking station in place);

(c) where the docking station comprises a filler structure (e.g., attached to a surface of the three-dimensional (3D) woven fabric), then implanting the docking station at the native heart valve can include implanting the docking station such that the filler structure helps inhibit paravalvular leakage;

(d) delivering the docking station to the native heart valve while the docking station is held in a compressed configuration inside a delivery catheter before implanting the docking station at the native heart valve;

(e) expanding the docking station from the compressed configuration to an expanded configuration (e.g., to implant the docking station at the native heart valve); and/or (f) where the prosthesis/bioprosthesis is a transcatheter heart valve (THV), delivering the THV to the docking station at the native heart valve while held inside a THV delivery catheter (e.g., in a compressed or delivery configuration) before implanting the THV inside the docking station;

(g) expanding the THV from a compressed/delivery configuration to an expanded or deployed configuration inside the docking station such that forces between the docking station and the prosthesis/bioprosthesis help to secure the prosthesis/bioprosthesis in the native heart valve.

Other steps described or implied elsewhere in this disclosure can also be included.

BRIEF DESCRIPTION OF THE DRAWINGS

Various embodiments are depicted in the accompanying drawings for illustrative purposes, and should in no way be interpreted as limiting the scope of the inventions. In addition, various features of different disclosed embodiments can be combined to form additional embodiments, which are part of this disclosure. Throughout the drawings, reference numbers may be reused to indicate correspondence between reference elements.

FIGS. 3A and 3B are perspective views of exemplary docking devices similar to the docking device of FIG. 1, with a polymer foam coupled to an outer surface of the docking device and a tubular woven fabric covering the polymer foam in accordance with one or more embodiments.

FIG. 4 is a cutaway perspective view of a tubular woven fabric covering a polymeric foam in accordance with one or more embodiments.

DETAILED DESCRIPTION

Figure 1:
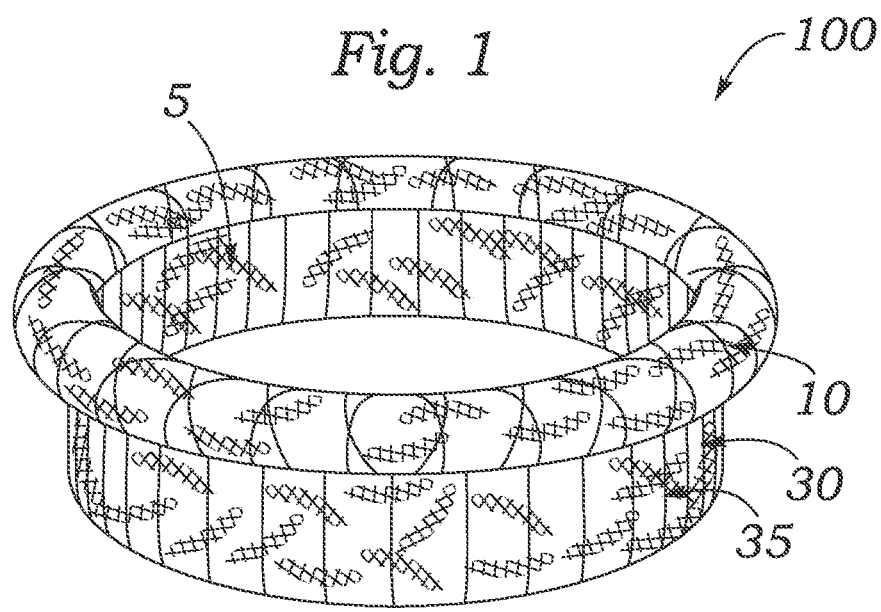
FIG. 1 is a perspective view of a docking device having three-dimensional (3D) woven fabric in accordance with one or more embodiments.

The headings provided herein are for convenience only and do not necessarily affect the scope or meaning of the claimed invention.

Although certain preferred embodiments and examples are disclosed below, inventive subject matter extends beyond the specifically disclosed embodiments to other alternative embodiments and/or uses and to modifications and equivalents thereof. Thus, the scope of the claims that may arise herefrom is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding some embodiments; however, the order of description should not be construed to imply that these operations are order dependent. Additionally, the structures, systems, and/or devices described herein may be embodied as integrated components or as separate components. For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

Overview

Docking devices and methods can utilize a woven or knitted fabric skirt material. In some implementations, textile skirts can be made by using polyethylene terephthalate (PET) in both warp and weft directions. However, generally, the PET material used may not have a shape memory effect that can change shape in connection with a trigger or stimulus, and may not be sufficiently elastic to provide for recovery after the deforming stress is removed. Therefore, it may be desirable to implement docking devices comprising fabrics and/or features that allow for improved flexibility with respect to shape or form. Some embodiments of docking devices disclosed herein are configured to adjust shape and/or form at least partially to the surrounding conditions/anatomy, and can take complex shapes to accommodate various different anatomies. In some implementations, the use of foam, polymer and/or biocompatible alloy with controlled diameter, size, and stiffness enables docking devices in accordance with the present disclosure to adjust and/or accommodate its shape or form to relatively complex anatomic geometries (e.g. different annulus sizes and/or shapes). That is, certain docking devices disclosed herein may be considered "universal" docking devices that provide desirable fit for a variety of sizes and/or shapes of patient anatomies.

Universal docking devices may be desired for use with certain implantable medical devices. For example, a universal docking device in accordance with the present disclosure can better conform to the complex anatomy associated with an implant site in some configurations. Furthermore, particularly with respect to prosthetic heart valve or bioprosthetic heart valves, universal docking devices in accordance with one or more embodiments of the present disclosure can help prevent paravalvular leakage and/or eliminate the need to carefully size the existing heart valves. With respect to these benefits, docking devices in accordance with one or more embodiments of the present disclosure can be configured to change shape and/or provide shape recovery after a deforming stress is removed, and can adjust to surrounding conditions to accommodate different complex anatomic geometries. Such attributes and/or characteristics can serve to at least partially mitigate paravalvular leakage.

Some embodiments disclosed herein provide a device that is configured and/or designed to improve the fit of an implantable prosthetic heart valve (e.g., an implantable bioprosthetic heart valve) within a native valve annulus, which can advantageously at least partially mitigate issues associated with valve sizing and/or paravalvular leakage. For example, generally, the unique and/or irregular size and/or surface characteristics of native valve annuli can present challenges to providing an implantable prosthetic/bioprosthetic heart valve that fits within, and is provided in intimate contact or seal with, the valve annulus. To address such challenges, some embodiments disclosed herein advantageously provide a tubular or cylindrically-shaped device that is radially compressible for delivery and implantation in the native valve annulus before implantation of a prosthetic/bioprosthetic valve.

The structure of tubular or cylindrically-shaped devices in accordance with the present disclosure can comprise both an inner three-dimensional (3D) woven fabric and an outer covering of polymeric foam. For example, the 3D woven fabric can comprise three different fibers and/or yarns having different material properties. Different types of fibers and/or yarns that may be used can include shape memory material, such as Nitinol, low-melt thermoplastic polymer or resin having a melting point in the range of about 166-175° C., such as Nylon, and high-tenacity biocompatible material, such as PET. Furthermore, the polymeric foam can be attached to the outer surface of the 3D woven fabric and can provide a compressible seal with the native annulus.

In some implementations, docking devices in accordance with the present disclosure can be manufactured to the desired shape at least in part by pressing and/or heating the 3D woven fabric over a shape-setting mold at temperatures above the melting point of the low-melt thermoplastic polymer or resin. The melting of low-melt material can function as an adhesive to set the shape of the fabric. After the desired shape of the 3D woven fabric is set, a foam material can be attached or sewed onto the 3-D woven fabric.

In some implementations, the present disclosure provides a method for fabricating a universal docking device, wherein a main body of the docking device is made of shape memory material (e.g., Ni—Ti alloy, Nitinol, or other shape memory material) and thermoplastic fibers by utilizing 3D weaving techniques. Such 3D weaving techniques may be implemented on a specialized 3D weaving machine. For example, in some 3D weaving implementations in accordance with embodiments of the present disclosure, three sets of yarns are used to interlace with each other, as compared to two sets of yarn in flat-woven structures. The weave can be orthogonal or multilayer, and multiple layers can be woven together to form a 3D fabric. In the width-wise (i.e., "filling" or "weft") direction, memory metal (e.g., Ni—Ti) round wire and low-melt Nylon can be used apart from high tenacity polyethylene terephthalate (PET). The melting temperature of the low-melt nylon resin can be designed to be in range of 166-175° C.

After weaving the fabric, methods of fabricating a docking device in accordance with one or more embodiments of the present disclosure can involve pressing the fabric over a shape-setting mold (e.g., having a specific custom shape) and heated for a period of time (e.g., 30-60 min) at temperatures higher than the melting point of the low-melt Nylon resin, thereby causing the low-melt nylon to melt. The melted Nylon can act as an adhesive, and can at least partially set the shape of the fabric. The method may further involve leaving the shape-set fabric on the mold to cool-off for a period of time (e.g., 1 hour), and then removing the shape-set fabric and covering the same with a tubular woven fabric filled with foam or other at least partially compressible material (e.g., polymer, biocompatible alloy, etc.). The optional use of foam, polymer or biocompatible alloy outside the device can advantageously help reduce paravalvular leakage as such material can be compressed during delivery to the annulus, and once deployment is complete, the material can at least partially decompress and form an improved seal. The optional use of tubular textile around the for or other compressible material can help control the porosity of such materials, as foam or polymeric materials can be undesirably porous; the outside textile (e.g., PET) covering can reduce permeability.

Universal Docking Device

With reference now to FIG. 1 of the illustrative drawings, there is shown a universal docking device 100 in accordance with one or more embodiments. The docking device 100 includes a three-dimensional (3D) woven fabric 10 forming an internal surface 5, an outer surface 35, and having a thickness therebetween provided by the 3D nature of the fabric 10. In one embodiment, the 3D woven fabric can form a substantially hollow cylinder 30 having an outer surface 35 and inner surface 5. In some embodiments, the 3D woven fabric can form a ring, or ring-type form or structure. Other shapes are also possible, depending on the prosthetic device or bioprosthetic device being docked within, or on, the docking device 100. In accordance with some implementations, the docking device 100 can be interposed between an implantable heart valve and a native valve annulus to provide an improved conforming fit and/or to reduce the likelihood and/or degree of a paravalvular leakage.

The 3D woven fabric 10 can be a hybrid fabric comprising two or more of the following: polyethylene terephthalate (PET), shape memory alloy or metal (e.g., Ni—Ti alloy, Nitinol, etc.), low-melt Nylon alloy, and/or other materials, cloths, polymers, etc. The 3D woven fabric 10 can be made using any suitable or desirable weaving technique and/or configuration/arrangement. For example, in the width-wise (i.e., "weft," "filling") direction, memory alloy or metal (e.g., Ni—Ti) round wire and low-melt Nylon can be used apart from high-tenacity PET, or the memory metal wire can be used entirely in the weft/filling direction in order to increase the shape memory effect of the fabric. The woven fabric structure 10 can be woven in 2D, 3D, and can be configured to fit any anatomical structure, by using the shape memory effect, or super elastic effect, of the memory metal wire or other material of the fabric. The woven fabric 10 can be configured to fit any desirable human anatomical part(s) through the use of shape memory alloy to change the shape of the mold. The fabric 10 can also be used in sheet form as a scaffold for tissue engineering with shape memory effect customized to any human anatomical shape.

In use, the docking device 100 can be compressed and delivered, such as through a catheter, to the implantation site. At the implantation site, the docking device 100 can be expanded to fit, and be held at, the local anatomy (e.g., the native heart valve annulus) associated with the implantation site. The docking device 100 can then act as a landing site for a prosthesis/bioprosthesis 200, such as a prosthetic heart valve (e.g., a transcatheter heart valve).

Figure 2:
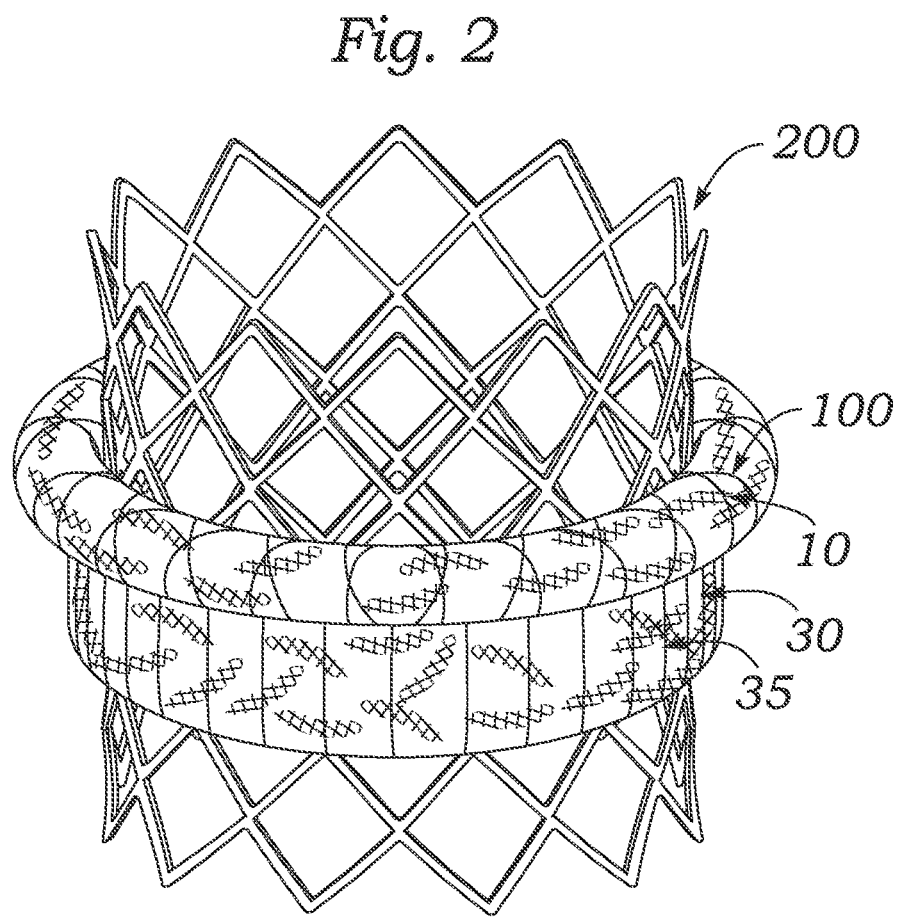
FIG. 2 is a perspective view of a frame of an exemplary transcatheter heart valve deployed inside the docking device of FIG. 1 in accordance with one or more embodiments.

FIG. 2 illustrates a perspective view of a frame 200 of an exemplary transcatheter heart valve deployed inside the docking device of FIG. 1 in accordance with one or more embodiments. With reference to FIG. 2, the docking device 100 can be interposed between a prosthesis/bioprosthesis 200, such as a transcatheter heart valve (THV), and native tissue, such as a native valve annulus (not shown). Optionally, some native tissue (e.g., leaflets, chordae, etc.) can be pinched between the docking device and prosthesis/bioprosthesis to better secure or anchor the combination in the desired location. Although FIG. 2 only shows the frame of an exemplary transcatheter heart valve 200 within the docking device 100, it should be understood that, in some implementations, other devices besides a THV can benefit from implantation within the docking device 200 and/or other docking devices in accordance with embodiments of the present disclosure.

The docking device 100 can be configured or designed to be implanted at any suitable or desirable implantation site. However, implantation sites of different patients can present relative irregularity of shapes across patients. By using shape memory effect for the fabric 10, the docking device 100 can be used to fit into irregular shapes. The device 100 can be configured to be compressed and delivered through a catheter to the implant site. At the delivery site, depending on whether using super-elastic shape memory metal or polymer is used, the device 100 can expand by itself or through temperature stimulus to fit the size of the implantation site anatomy (e.g., heart valve annulus). Foam or other compressible material (not shown in FIGS. 1 and 2) disposed on the outside of the device 110 can also advantageously fill the open space between the implantation site anatomy (e.g., annulus) and the device 100 to create an effective sealing. The docking device 100 can act as a landing site for the prosthetic heart valve.

FIGS. 3A and 3B are perspective views of the docking device 100 of FIG. 1, wherein the docking device 100, optionally, has a polymer foam 40 coupled to an outer surface 35 of the docking device 100 and a tubular woven fabric 45 covering the polymer foam 40 in accordance with one or more embodiments. As shown in FIGS. 3A and 3B, the docking device 100 can further include a filler 40 (also referred to herein as a "filler structure") coupled or coupleable to the outer surface 35 of the hollow cylinder 30. The filler 40 can comprise a polymeric foam. The polymeric foam can be an open-celled foam or a closed-cell foam. In some embodiments, the form or structure of filler 40 can be provided to partially or completely surround a circumference of the outer surface 35 of the hollow cylinder 30. In some embodiments, the filler 40 can include a compressible or expandable material that can fill a desired space. In some embodiments, the filler 40 can be or comprise a polymer foam. In some embodiments, the filler 40 can comprise medical-grade silicone and/or a biocompatible alloy. In some embodiments, the filler can comprise one or more of polymeric foam, polyurethane foam, polyvinyl chloride foam, Styrofoam, polyimide foam, silicone foam, microcellular foam, and/or another type of filler.

The filler structure 40 can be configured to be compressed during delivery of the docking device 100 to the implantation site (e.g., valve annulus). Once deployed, the filler 40 can be configured to decompress to provide a compressible seal against the surrounding native tissue. This compressible seal can be optimized by varying the shape, size, and stiffness of the filler 40. For example, the filler 40 can be configured, as shown in FIG. 3A, to cover a portion of the outer surface 35 of the hollow cylinder 30. Alternatively, the filler can be configured, as shown in FIG. 3B, to cover substantially all, or at least a majority, of the outer surface 35. In this way, the configuration of the filler 40 can be optimized to enable the docking device 100 to accommodate itself to complex anatomic geometries and/or, in the case of a prosthetic heart valve, to reduce paravalvular leakage.

In some embodiments, the filler 40 can be dimensioned to cover at least 10%, at least 20%, at least 30%, at least 40%, at least 50%, at least 60%, at least 70%, at least 80%, at least 90%, or 100% of the outer surface 35 of the hollow cylinder 30. In some embodiments, the filler can also be dimensioned to cover a percentage of the outer surface that includes and is between any two of the foregoing values.

FIG. 4 is a cutaway perspective view of a tubular woven fabric 45 covering a polymeric foam 40 in accordance with one or more embodiments. In some embodiments, the filler component/structure of a docking device in accordance with aspects of the present disclosure comprises a material that is, by itself, too porous to fully prevent or mitigate paravalvular leakage. Accordingly, with reference to FIG. 4, in some embodiments, the filler 40 can be covered with a tubular woven fabric 45, such as PET. In some embodiments, the filler 40 can be secured to a docking device, such as the docking device 100 shown in FIGS. 3A and 3B, by attaching the tubular woven fabric 45 to the outer surface 35 of the docking device's hollow cylinder 30. For example, the tubular woven fabric 45 may be attached to the outer surface 35 by adhering or suturing the tubular woven fabric 45 directly to the outer surface 35. So configured, the tubular woven fabric 45, with its low porosity and reduced permeability, can further mitigate paravalvular leakage. The tubular woven fabric 45 can also be provided to protect or ensure against the release of any undesired particulate matter from the filler 40, particularly with respect to embodiments in which the filler 40 is made of a porous and/or a foam material. Such particulate matter can be released due to the frictional forces imposed on the filler 40 during the delivery and/or implantation process(es). Release of such particulate matter can be undesirable as presenting a higher risk of embolization.

3D Woven Fabric

In some implementations, the present disclosure is related to relatively complex textile structures generated by utilizing weaving, braiding, knitting and/or a combination thereof. Such textiles structures can be generated using shape memory fibers or alloys (e.g., Nitinol) in combination with one or more thermoplastic textile fibers, such as Nylon, polyethylene terephthalate (PET), polypropylene (PP), polybutylene terephthalate (PBT), etc. Hybrid textile structures in accordance with the present disclosure can be created using a base substrate fabric, and using electro-spinning to lay shape memory fibers on top of the substrate fabric, or by wrapping a low-melt Nylon in a core-sheath structure. As described above, the textile structure can be formed into a hollow cylinder form, wherein the outside of the cylinder form is at least partially enveloped by foam, polymer (e.g. medical-grade silicone), and/or a biocompatible alloy.

Devices in accordance with some implementations can include a three-dimensional (3D) woven fabric that is formed into a hollow cylinder, as well as a polymer foam attached to the hollow cylinder. The 3D woven fabric can advantageously comprise three different types of yarns or fibers, as described in detail herein. For example, the 3D woven fabric can comprise one or more of the following types of yarns and/or fibers: shape memory material, low-melt thermoplastic polymer or resin, and high-tenacity biocompatible material.

Example embodiments of 3D woven fabrics for use with docking devices are described below. As described above, 3D woven fabrics in accordance with embodiments of the present disclosure can comprise three different types of fibers or yarns. In some embodiments, the three different types of fibers or yarns can comprise a combination of a shape memory material, a low-melt thermoplastic polymer or resin, and a high-tenacity biocompatible material. In some embodiments, the shape memory material can be or comprise a metal alloy. The metal alloy can comprise nickel and/or titanium, such as Nitinol. In one embodiment, the shape memory material can provide the desired shape and geometry of the device.

With respect to the low-melt thermoplastic polymer or resin material, in some embodiments, such material can act as a binder or glue to fuse woven layers of the 3D fabric 10 together and conform the 3D woven fabric 10 to a desired shape. In some embodiments, the low-melt thermoplastic polymer or resin can be or comprise Nylon, for example.

The low-melt thermoplastic polymer or resin can have a relatively low-melting point. In accordance with an optional aspect, the low-melting point of the low-melt thermoplastic polymer or resin can be 200° C. or less, 195° C. or less, 190° C. or less, 185° C. or less, 180° C. or less, 175° C. or less, 170° C. or less, 165° C. or less, 160° C. or less, 155° C. or less, 150° C. or less, 145° C. or less, 140° C. or less, 135° C. or less, 130° C. or less, 125° C. or less, 120° C. or less, 115° C. or less, 110° C. or less, 105° C. or less, and 100° C. or less. The low-melting point can be within a range that includes and is between any two of the foregoing values.

With respect to the high-tenacity biocompatible material, such material can improve the durability of the 3D woven fabric 10 and promote tissue growth. In some embodiments, the high-tenacity biocompatible material can have a tenacity, or breaking load, of about 5 grams per Denier or more, about 6 grams per Denier or more, about 7 grams per Denier or more, about 8 grams per Denier or more, about 9 grams per Denier or more, about 10 grams per Denier or more, about 11 grams per Denier or more, about 12 grams per Denier or more, about 13 grams per Denier or more, about 14 grams per Denier or more, or about 15 grams per Denier. The breaking load can also be within a range that includes and/or is between any two of the foregoing values. In some embodiments, the high-tenacity biocompatible material can be PET.

In another embodiment, methods for making a docking device 100 for a prosthesis 200 (e.g., for a bioprosthesis) are described. One such method comprises weaving a 3D woven fabric 10 by interlacing a shape memory material, a low-melt thermoplastic polymer or resin, and a high-tenacity biocompatible material. The shape memory material can be a metal alloy. The metal alloy can comprise nickel and titanium, such as Nitinol. The low-melt thermoplastic polymer or resin can be a polymer having a low-melting point. The polymer can be nylon. The high-tenacity biocompatible material can be PET.

3D woven fabrics can generally be woven by manipulating yarns in the length ("warp," or "ends"), width ("weft," "filling," or "picks"), and through-the-thickness directions. In some embodiments, the combination of the low-melt thermoplastic polymer and the 3D weave pattern can allow the thickness of the 3D woven fabric to be varied based on the number of layers of the weft and warp yarns. Thus, in one aspect, the thickness of the 3D woven fabric can be increased by increasing the number of layers of the weft and warp yarns with the low-melt thermoplastic polymer and the through-the-thickness yarns binding the plurality of layers together.

The through-the-thickness yarn can be incorporated at varying levels and angles within orthogonal (FIG. 5A), multilayer (FIG. 5B), and angle-interlock (FIG. 5C) woven structures to obtain desired mechanical properties. The weaving step can be performed on conventional weaving machines or specially-made weaving machines. In some embodiments, braiding or knitting techniques can be employed to manufacture the 3D fabric. However, in some implementations, such methods may not produce sufficient thickness.

Figure 5A:
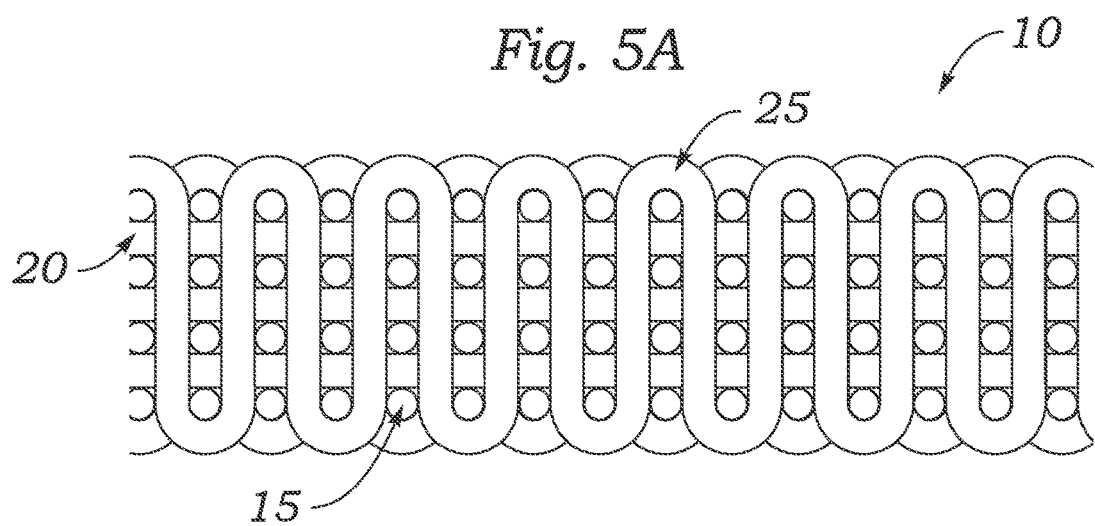
FIG. 5A is a cross-sectional schematic view of a 3D orthogonal woven unit cell in accordance with one or more embodiments.

With reference to FIG. 5A, in one embodiment, the 3D woven fabric 10 can comprise an orthogonal weave structure. Orthogonal weave structures can include a set of warp yarns 15, a set of filling yarns 20, and a set of through-the-thickness yarns 25. Warp yarns 15 can be placed in the fabric length direction and filling yarns 20 can be inserted between the length layers to form double picks. Through-the-thickness yarns 25 can interconnect the other two yarn sets and provide structural integrity. The thickness of the orthogonal structure can be formed by the number of layers of the warp or weft yarn. In some embodiments, yarns are substantially straight in the warp, weft, and through-the-thickness directions. The through-the-thickness yarns can generally travel vertically between the top and bottom weft yarn layers, and can also interlink with weft yarn layers at other levels in some embodiments.

In some embodiments, the 3D woven fabric 10 can comprise an orthogonal weave structure, wherein the set of warp yarns 15 can comprise a shape memory material, the set of filling yarns 20 can comprise a low-melt thermoplastic polymer or resin, and the set of through-the-thickness yarns 25 can comprise a high-tenacity biocompatible material.

In some embodiments, the 3D woven fabric 10 can comprise an orthogonal weave structure, wherein the set of warp yarns 15 can comprise a high-tenacity biocompatible material, the set of filling yarns 20 can comprise a shape memory material, and the set of through-the-thickness yarns 25 can comprise a low-melt thermoplastic polymer or resin.

Figure 5B:
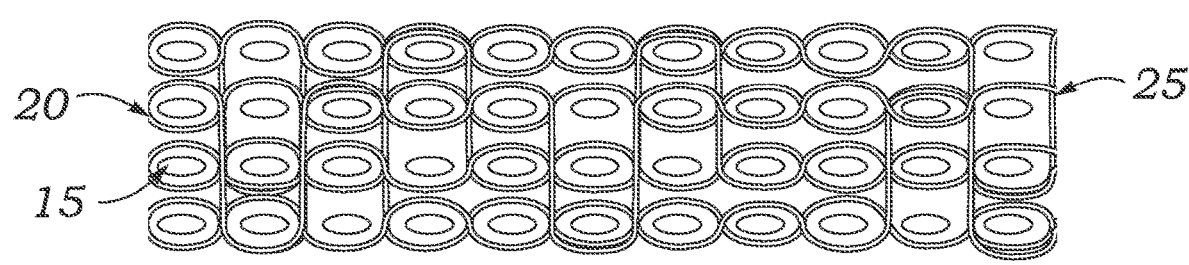
FIG. 5B is a cross-sectional schematic view of a 3D multilayer woven unit cell in accordance with one or more embodiments.

With reference to FIG. 5B, in some embodiments, the 3D woven fabric 10 can comprise a multilayer weave structure. Multilayer weave structures can include a set of warp yarns 15, a set of weft yarns 20, and a set of through-the-thickness binding yarns 25. Warp yarns 15 can be interlaced with weft yarns 20 at each layer according to the weave pattern in in-plane principal directions, whereas binding yarns 25 can be interlaced with warp yarns 15 at each layer according to the weave pattern in out-of-plane principal directions. The multilayer weave structure can be fully interlaced or semi-interlaced.

In some embodiments, the 3D woven fabric 10 can comprise a multilayer weave structure, wherein the set of warp yarns 15 can comprise a shape memory material, the set of weft yarns 20 can comprise a low-melt thermoplastic polymer or resin, and the set of binding yarns 25 can comprise a high-tenacity biocompatible material.

In some embodiments, the 3D woven fabric 10 can comprise a multilayer weave structure, wherein the set of warp yarns 15 can comprise a high-tenacity biocompatible material, the set of weft yarns 20 can comprise a shape memory material, and the set of binding yarns 25 can comprise a low-melt thermoplastic polymer or resin.

Figure 5C:
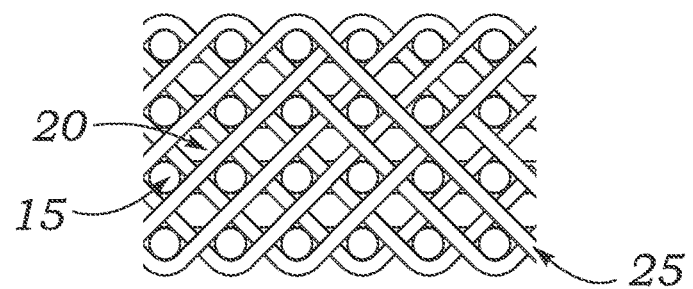
FIG. 5C is a cross-sectional schematic view of a 3D angle-interlock woven unit cell in accordance with one or more embodiments.

With reference to FIG. 5C, in some embodiments, the 3D woven fabric 10 comprises an angle-interlock weave structure. Angle-interlock weave structures in accordance with the present disclosure can include a set of warp yarns 15, a set of straight weft yarns 20 (wadding), and a set of bias weft yarns 25 that weave with the warp yarns 15 in a diagonal direction in the thickness. In layer-to-layer angle-interlock weaves (not shown), bias weft yarns 25 can travel between two or more successive layers making interlacements with several wadding yarns 20 according to the weave pattern. In through-thickness angle-interlock weaves (FIG. 5C), bias weft yarns 25 can bind diagonally from the top layer to the bottom layer.

In some embodiments, the 3D woven fabric 10 can comprise an angle-interlock structure, wherein the set of warp yarns 15 can comprise a shape memory material, the set of straight weft yarns 20 can comprise a low-melt thermoplastic polymer or resin, and the set of bias weft yarns 25 can comprise a high-tenacity biocompatible material.

In some embodiments, the 3D woven fabric 10 can comprise an angle-interlock structure, wherein the set of warp yarns 15 can comprise a high-tenacity biocompatible material, the set of straight weft yarns 20 can comprise a shape memory material, and the set of bias weft yarns 25 can comprise a low-melt thermoplastic polymer or resin.

It should be understood that other varieties of 3D weave structures, including different varieties of orthogonal, multilayer, and angle-interlock weave structures, may be used in connection with embodiments of the present disclosure. To optimize the physical characteristics of the docking device 100 for use with a particular prosthesis/bioprosthesis 200 or installation site, the 3D woven fabric 10 can be manufactured using any of the different varieties of 3D weave structures.

For example, in use with a prosthetic/bioprosthetic heart valve, the docking device 100 may be subjected to compressive forces between the prosthesis/bioprosthesis 200 and the surrounding native valve tissue. The compressibility of the docking device 100 can be, in part, a function of the compressibility of the 3D woven fabric, which can, in turn, be a function of the fabric's weave structure, fabric density, and/or other characteristics of the constituent fibers/yarns. Accordingly, the 3D woven fabric's 10 weave structure and fabric density can be selected to optimize the compressibility of docking device 100.

Fabric density can be quantified by ends-per-inch (EPI) and/or picks-per-inch (PPI). In some embodiments, the 3D woven fabric 10 can have about 115 EPI, about 120 EPI, about 125 EPI, about 130 EPI, about 135 EPI, about 140 EPI, about 145 EPI, about 150 EPI, about 155 EPI, about 160 EPI, about 165 EPI, about 170 EPI, about 175 EPI, about 180 EPI, about 185 EPI, about 190 EPI, about 195 EPI, about 200 EPI, about 205 EPI, about 210 EPI, about 215 EPI, about 220 EPI, about 225 EPI, about 230 EPI, about 235 EPI, about 240 EPI, about 245 EPI, about 250 EPI, about 255 EPI, about 260 EPI, about 265 EPI, about 270 EPI, about 275 EPI, about 280 EPI, about 285 EPI, about 290 EPI, about 295 EPI, about 300 EPI, about 305 EPI, about 310 EPI, about 315 EPI, about 320 EPI, about 325 EPI, about 330 EPI, about 335 EPI, about 340 EPI, about 345 EPI, or about 350 EPI. In some embodiments, the 3D woven fabric 10 can have ends-per-inch between and including any two of the foregoing values.

In one embodiment, the 3D woven fabric 10 can have about 115 PPI, about 120 PPI, about 125 PPI, about 130 PPI, about 135 PPI, about 140 PPI, about 145 PPI, about 150 PPI, about 155 PPI, about 160 PPI, about 165 PPI, about 170 PPI, about 175 PPI, about 180 PPI, about 185 PPI, about 190 PPI, about 195 PPI, about 200 PPI, about 205 PPI, about 210 PPI, about 215 PPI, about 220 PPI, about 225 PPI, about 230 PPI, about 235 PPI, about 240 PPI, about 245 PPI, about 250 PPI, about 255 PPI, about 260 PPI, about 265 PPI, about 270 PPI, about 275 PPI, about 280 PPI, about 285 PPI, about 290 PPI, about 295 PPI, about 300 PPI, about 305 PPI, about 310 PPI, about 315 PPI, about 320 PPI, about 325 PPI, about 330 PPI, about 335 PPI, about 340 PPI, about 345 PPI, or about 350 PPI. In some embodiments, the 3D woven fabric 10 can have picks-per-inch between and including any two of the foregoing values.

In some embodiments, the docking device 100 exhibits a compressibility of no more than 5%, no more than 10%, no more than 15%, no more than 20%, no more than 25%, no more than 30%, no more than 35%, no more than 40%, no more than 45%, no more than 50%, no more than 55%, no more than 60%, no more than 65%, or no more than 70% across its thickness. In some embodiments, the docking device can exhibit a compressibility of between and including any two of the foregoing values.

Figure 6:
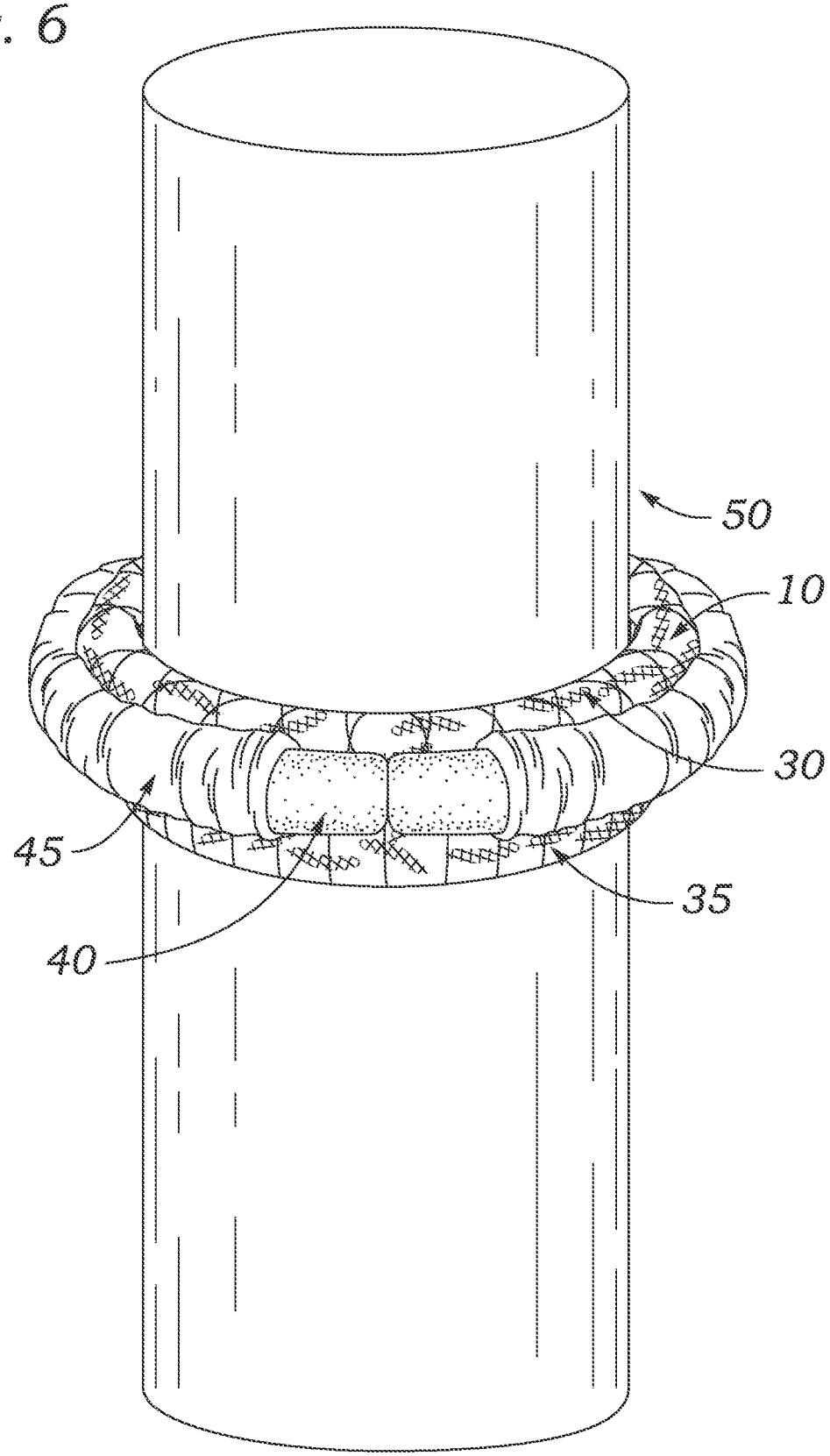
FIG. 6 is a perspective view of the docking device of FIG. 1 in a shape setting mandrel in accordance with one or more embodiments.

With reference to FIG. 6, a method for making a docking device 100 for a prosthesis (e.g., for a bioprosthesis) can comprise the step of pressing and heating the 3D woven fabric 10 over a shape-setting mold 50 at temperatures greater than the melting point of the low-melt thermoplastic polymer or resin. This step can melt the low-melt thermoplastic polymer or resin yarn, which can function as an adhesive to set the shape of the 3D woven fabric 10 as desired. In some embodiments, the 3D woven fabric 10 can be heated on the shape-setting mold 50 from about 30 minutes to about 60 minutes. In some embodiments, the prosthesis or bioprosthesis can be a transcatheter heart valve, and the 3D woven fabric 10 can be molded accordingly. It should be understood, however, that the 3D woven fabric 10 can be molded to accommodate other prostheses/bioprostheses, or as a scaffold for tissue engineering.

In some embodiments, the method can further comprise the step of attaching a filler 40 to a surface 35 of the 3D woven fabric 10, for example by sewing the filler 40 to the surface 35 of the 3D woven fabric 10. In a further embodiment, the method can include the step of covering the filler 40 with a tubular woven fabric 45 comprising, for example, polyethylene terephthalate (PET). In some embodiments, the filler 40 can be a polymer foam.

It should be appreciated from the foregoing description that the present invention provides a universal docking device that can be radially compressible, for delivery and implantation, and that changes shape and recovers after a deforming stress is removed. The docking device adjusts to surrounding conditions to accommodate different complex anatomic geometries, and provides conforming support while minimizing or eliminating leakage around the implanted device.

The invention has been described in detail with reference only to the presently preferred embodiments. Persons skilled in the art will appreciate that various modifications can be made without departing from the invention. Accordingly, the invention is defined only by the following claims.

Additional Embodiments

Depending on the embodiment, certain acts, events, or functions of any of the processes described herein can be performed in a different sequence, may be added, merged, or left out altogether. Thus, in some embodiments, not all described acts or events are necessary for the practice of the processes. Moreover, in some embodiments, acts or events may be performed concurrently.

Conditional language used herein, such as, among others, "can," "could," "might," "may," "e.g.," and the like, unless specifically stated otherwise, or otherwise understood within the context as used, is intended in its ordinary sense and is generally intended to convey that some embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous, are used in their ordinary sense, and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Conjunctive language such as the phrase "at least one of X, Y and Z," unless specifically stated otherwise, is understood with the context as used in general to convey that an item, term, element, etc. may be either X, Y or Z. Thus, such conjunctive language is not generally intended to imply that some embodiments require at least one of X, at least one of Y and at least one of Z to each be present.

It should be appreciated that in the above description of embodiments, various features are sometimes grouped together in a single embodiment, Figure, or description thereof for the purpose of streamlining the disclosure and aiding in the understanding of one or more of the various inventive aspects. This method of disclosure, however, is not to be interpreted as reflecting an intention that any claim require more features than are expressly recited in that claim. Moreover, any components, features, or steps illustrated and/or described in a particular embodiment herein can be applied to or used with any other embodiment(s). Further, no component, feature, step, or group of components, features, or steps are necessary or indispensable for each embodiment. Thus, it is intended that the scope of the inventions herein disclosed and claimed below should not be limited by the particular embodiments described above, but should be determined only by a fair reading of the claims that follow.

What is claimed is:

1. A docking device for a prosthesis, the docking device comprising:
    a three-dimensional (3D) woven fabric forming a shaped element having an internal surface, an outer surface, and a thickness therebetween, the 3D woven fabric comprising a multilayer weave structure including a set of warp yarns comprising a first type of fiber, a set of weft yarns comprising a second type of fiber, and a set of through-the-thickness binding yarns comprising a third type of fiber; and
    a filler structure coupled to the outer surface of the shaped element;
    wherein:
        the first type of fiber comprises a first one of a group consisting of shape memory material, low-melt thermoplastic polymer or resin, and high-tenacity biocompatible material;
        the second type of fiber comprises a second one of the group; and
        the third type of fiber comprises a third one of the group.

2. The docking device of claim 1, wherein the prosthesis is a transcatheter heart valve.

3. The docking device of claim 1, wherein the shape memory material comprises nitinol.

4. The docking device of claim 1, wherein the low-melt thermoplastic polymer or resin has a melting point between 85 degrees Celsius and 200 degrees Celsius.

5. The docking device of claim 4, wherein the low-melt thermoplastic polymer or resin comprises nylon.

6. The docking device of claim 1, wherein the high-tenacity biocompatible material comprises polyethylene terephthalate (PET).

7. The docking device of claim 1, wherein the filler structure is covered with a material having low porosity.

8. A docking device comprising:
    a three-dimensional (3D) woven fabric forming a shaped element having an internal surface, an outer surface, and a thickness therebetween, the 3D woven fabric comprising a multilayer weave structure including a set of warp yarns, a set of weft yarns, and a set of through-the-thickness binding yarns; and
    a filler structure coupled to the outer surface of the shaped element and comprising polymer foam.

9. The docking device of claim 8, wherein the polymer foam is at least partially covered with a tubular woven fabric.

10. The docking device of claim 9, wherein the tubular woven fabric comprises polyethylene terephthalate (PET).

11. The docking device of claim 8, wherein:
    each of the set of warp yarns is interlaced with a plurality of the set of weft yarns in each layer according to a weave pattern in in-plane principal directions; and
    each of the set of through-the-thickness binding yarns is interlaced with a plurality of the set of weft yarns in each layer according to the weave pattern in out-of-plane principal directions.

12. The docking device of claim 8, wherein the multilayer weave structure is fully interlaced.

13. The docking device of claim 8, wherein the multilayer weave structure is semi-interlaced.

14. The docking device of claim 8, wherein the set of warp yarns, the set of weft yarns, and the set of through-the-thickness binding yarns comprise first, second, and third different types of fibers, respectively.

15. The docking device of claim 14, wherein the set of warp yarns comprises a shape memory material, the set of weft yarns comprises a low-melt thermoplastic polymer or resin, and the set of through-the-thickness binding yarns comprises a high-tenacity biocompatible material.

16. The docking device of claim 14, wherein the set of warp yarns comprises a high-tenacity biocompatible material, the set of weft yarns comprises a shape memory material, and the set of through-the-thickness binding yarns comprises a low-melt thermoplastic polymer or resin.

* * * * *